United States Patent [19]

Becker

[11] Patent Number: 5,009,896
[45] Date of Patent: Apr. 23, 1991

[54] MULTI-FRACTIONABLE TABLET STRUCTURE

[75] Inventor: John W. Becker, Littleton, Colo.

[73] Assignee: Akzo N.V., Arnhem, Netherlands

[21] Appl. No.: 416,902

[22] Filed: Oct. 4, 1989

[51] Int. Cl.$^5$ .............................................. A61K 9/44
[52] U.S. Cl. ..................................... 424/467; D28/1;
 D28/2; D28/3; D28/8.1; D1/121; D1/128
[58] Field of Search ........................ D28/1, 2, 3, 8.1;
 D1/121, 128; 424/467

[56] References Cited

U.S. PATENT DOCUMENTS

| D. 34,312 | 4/1901 | Ewell et al. | D28/8.1 |
|---|---|---|---|
| D. 47,061 | 3/1915 | Ward | D1/121 |
| D. 49,942 | 11/1916 | Ward | D1/121 |
| D. 50,810 | 5/1917 | Geis | D1/121 |
| D 50,827 | 5/1917 | Ward | D1/121 |
| D. 50,925 | 6/1917 | Ward | D1/121 |
| D 99,993 | 6/1936 | Brooks | D1/121 |
| D. 100,257 | 7/1936 | Brooks | D1/121 |
| D. 212,274 | 9/1968 | Evans | D1/121 |
| D. 228,456 | 9/1973 | Ninger | D1/121 |
| D. 262,663 | 1/1982 | Nev et al. | D28/8.1 |
| D. 269,719 | 7/1983 | Tovey | D28/8.1 |
| D. 283,739 | 5/1986 | Tovey | D28/8.1 |
| 4,215,104 | 7/1980 | Ullman et al. | |
| 4,258,027 | 3/1981 | Ullman et al. | |
| 4,353,887 | 10/1982 | Hess et al. | 424/467 |
| 4,824,677 | 4/1989 | Shah et al. | 424/467 |

FOREIGN PATENT DOCUMENTS

| 352208 | 11/1937 | Italy | 424/467 |
|---|---|---|---|
| 8869 | of 1888 | United Kingdom | 424/467 |
| 189400 | 11/1922 | United Kingdom | 424/467 |
| 993291 | 5/1965 | United Kingdom | 424/467 |

Primary Examiner—Shep K. Rose
Attorney, Agent, or Firm—William M. Blackstone; Donna Bobrowicz

[57] ABSTRACT

A pharmaceutical tablet that is readily divisible into sub-dosage units of two and three equal parts, said tablet comprising two surfaces on opposite sides of the tablet each having scoremarkings thereon, the scoremarkings on the one surface dividing the tablet into two equal parts and the scoremarkings on the second surface dividing the tablet into three equal parts, said tablet having an approximately triangular cross section in the plane of said scoremarked surfaces.

7 Claims, 2 Drawing Sheets

MULTI-FRACTIONABLE TABLET STRUCTURE

The present invention relates to a tablet structure comprising two planar surfaces constituting a unitary dose, which structure is easily divided into two or three equal sub-dosage units through scoremarkings.

BACKGROUND OF THE INVENTION

It is well known in the art that tablets may comprise grooves or scoremarkings to facilitate breakage. Circular tablets easily severable into halves are described in U.S. Pat. No. 3,883,647. A circular tablet said to be dividable into quarters is disclosed in U.S. Pat. No. 3,723,614, which tablet comprises scoremarkings resembling a maltese cross.

In U.S. Pat. No. 4,215,104 an approximately rectangular tablet is disclosed, which comprises one or two transverse scoremarkings on each opposite side and two, respectively one transverse scoremarking on the two sides connecting the opposite sides. In one embodiment the rectangular tablet comprises one longitudinal scoremarking on one side and two transversely positioned scoremarkings on the opposite side.

These diverse attempts to improve the convenience and accuracy of breaking a grooved tablet have achieved only limited success. Circular tablets are frequently difficult to grasp for purposes of breaking. This problem can be overcome partially, but not completely, with the rectangular tablets of U.S. Pat. No. 4,215,104.

If doses equivalent to one third of the tablet are to be administered, some difficulties arise. After breaking off the first third, the length of the tablet is reduced to two thirds of the original length. This makes the tablet more difficult to grasp and break. A typical attempt to sever the remaining two thirds of the tablet is by means of a sharp knife, which on the one hand often results in fracture of the tablet into undesirable small pieces and which on the other hand often results in both sections being propelled away from the initial location because of the pressure applied to the scoremarking. These drawbacks are circumvented with the tablets of the present invention.

SUMMARY OF THE INVENTION

The present invention provides a tablet structure that can easily be divided into halves or thirds. The tablet is approximately triangular in shape, with scoremarkings positioned on the two opposite triangular planar surfaces.

Generally, the scoremarkings for breaking the structure into halves will be positioned on the planar surface opposite the surface where the scoremarkings for breaking the structure into thirds are positioned.

In a preferred embodiment the tablet according to the invention comprises one scoremarking for breaking the tablet into halves and two scoremarkings on the opposite surface for breaking the tablet into equal thirds.

The positioning of the scoremarkings is particularly easy when the three sides and angles of the triangular shape are equal. By choosing an equilateral triangle shaped tablet, the scoremarkings can be positioned in a manner such that, after breaking off one third, the width of the tablet remains the same, so that ease of handling is not diminished.

For very large tablets, ease of swallowing may be enhanced by reducing two of the angles of the triangular shape.

BRIEF DESCRIPTION OF THE DRAWINGS

The invention will be more specifically described in one of its embodiments in FIGS. 1a, 1b and 2.

In FIG. 1a, (1) indicates the planar surface, with beveled edges (2) at the borders and scoremarking (3) extending perpendicularly from the midpoint of the lower side to a distance from the edge approximately one-half the length of said side, where it intersects scoremarking (4), which crosses the tablet transversely.

The dotted line 9 indicates the scoremarking present on the opposite planar surface.

Figure 1A:
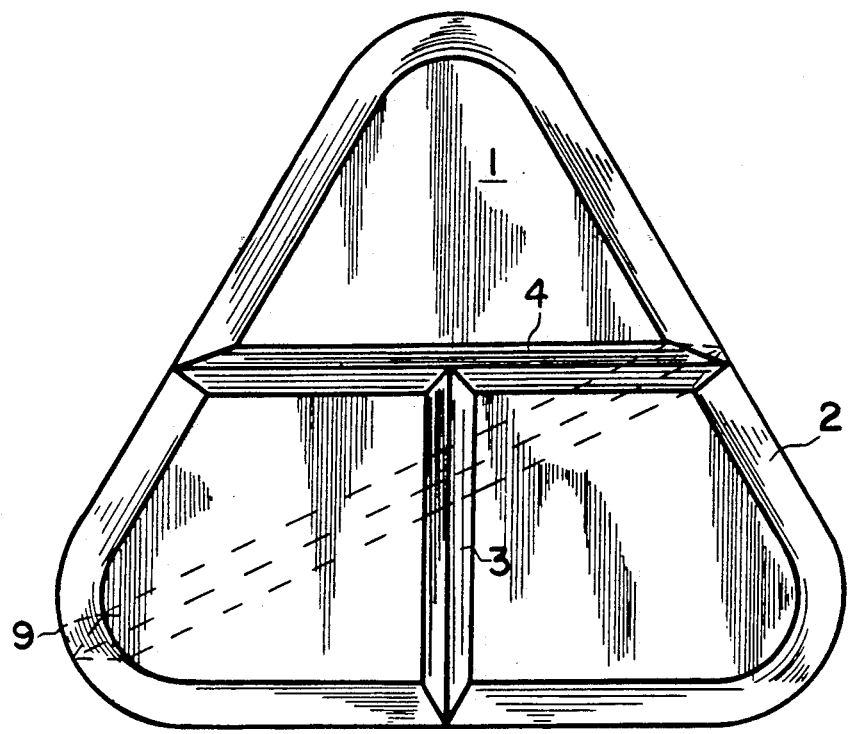
FIG. 1a is a top view of a tablet according to the invention.
Figure 1B:
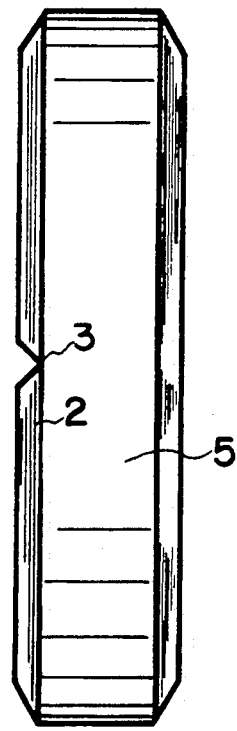
FIG. 1b is a side view of the same tablet.

FIG. 1b shows a side view wherein (5) is the approximately vertical side wall with a beveled edge (2) at its border and scoremarking (3) in the middle.

Figure 2:
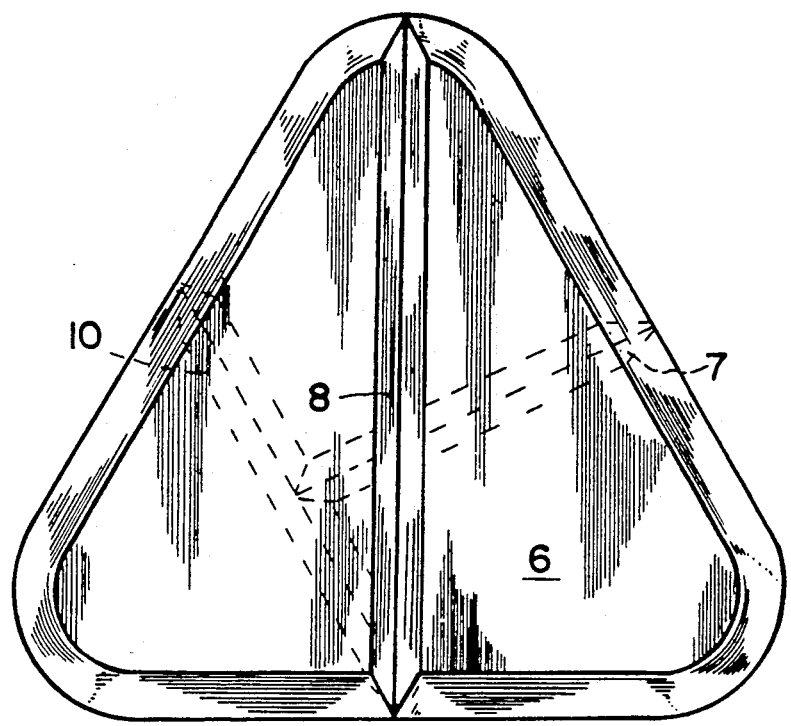
FIG. 2 is a bottom view of the tablet of FIG. 1.

FIG. 2 shows planar surface (6) of the bottom with beveled edges (7) and scoremarking (8).

The dotted line 10 indicates the scoremarking present on the opposite planar surface.

Figure 3A:
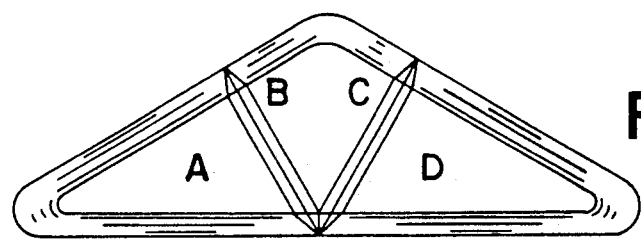
FIG. 3 is another embodiment of a tablet according to the invention.
Figure 3B:
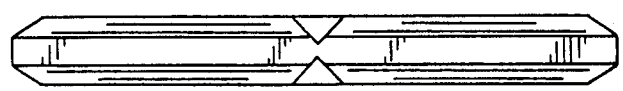
Figure 3C:
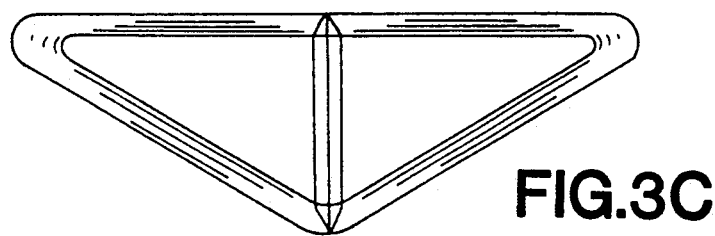

FIG. 3 shows another triangular tablet with the scoremarkings positioned as indicated. The position of the scoremarkings is such that area A equals area D, which equals areas B+C.

DESCRIPTION OF THE PREFERRED EMBODIMENTS

A tablet structure with three equal angles with especially positioned scoremarkings for breaking the tablet into equal bisectional and trisectional sub-dosage units is represented in FIGS. 1 and 2.

One tablet surface (FIG. 1) comprises a first scoremarking extending from the midpoint of one of the sides of the triangle for a distance equivalent to one-half of the length of that side, and a second scoremarking positioned at the end of the first scoremarking perpendicular to it.

The other planar surface comprises a scoremarking extending from the corner opposite the side where the first scoremarking extends from midpoint thereof, to the midpoint of that side, dividing the second surface into two equal portions.

If the scoremarkings are positioned in this manner, the first scoremarking is directly opposite the scoremarking on the other planar surface. This enhances the ease in breaking the tablet into halves. However, for breaking the tablet into thirds, it must broken at the perpendicular scoremarking before breaking it at the two parallel scoremarkings. Mistakes are liable to be made because of the parallel scoremarking on the other side of the tablet, which will be easily accidentally broken into halves. Therefore another useful embodiment comprises the same two scoremarkings as described hereinbefore on one planar surface, and on the other planar surface a scoremarking that extends from a corner adjacent to the side from the midpoint of which the first scoremarking extends to the midpoint on the side opposite said corner.

Such a tablet will still be readily divided into halves and thirds, but errors in choosing the wrong scoremarking are avoided.

Another embodiment of the triangular tablet according to the invention is shown in FIG. 3. The tablet is an equilateral or isosceles triangle capable of being divided into halves or thirds. The scoremarkings on one surface are located such that area A = area D = area B + area C. The opposite surface has a single scoremarking dividing the tablet into equal halves. The gripping surface for manually fracturing the tablet can be increased by making the equal angles of the isosceles triangle more acute.

The two planar surfaces may be flat, concave, convex or irregular. Usually these surfaces will be joined at the edges by more or less vertical walls, although this is not absolutely necessary. Both surfaces may be concave or convex, or one surface may be convex and the other concave. In this embodiment the edges of the tablet are nearly semicircular. Other embodiments may also have curved edges.

If an embodiment including approximately vertical walls is chosen, the planar surfaces may include beveled edges. For ease of production, the scoremarkings may have an indentation to the depth of the line defining the beveled edges. The beveled edge angle may be any angle between about 10° and 80°; typically 30° to 60°.

For ease of swallowing, the corners and sides of the triangular tablet structure may be rounded-off or otherwise smoothed to avoid sharp corners and edges.

The scoremarkings may vary widely in size and shape. However, good results have been obtained with scoremarkings having a V-groove angle of about 40° to about 120°, with a groove depth of about 1/20 to ½ of the thickness of the tablet.

Of course, if both surfaces comprise collinear scoremarkings opposite each other, as represented in FIGS. 1 and 2, the groove depth should be less than ½ of the thickness of the tablet.

Tablets of the invention may comprise a variety of active and inert ingredients, which are well known to one skilled in the art. They include, among others, fillers, lubricants, carriers, flavoring ingredients and, of course, active pharmaceutical ingredients. Many pharmaceutically active ingredients are suitable to be incorporated into multi-dosage tablets, such as anti-inflammatory agents, anti-depressive agents, anesthetics, and etc.

We claim:

1. A pharmaceutical tablet that is readily divisible into sub-dosage units of two or three equal parts, said tablet comprising (i) an equilateral or isosceles triangle shape, (ii) two opposite triangular planar surfaces each having scoremarkings thereon, (iii) the scoremarkings on one surface consisting of a first scoremarking extended perpendicularly from the midpoint of one edge of the triangle and a second scoremarking positioned perpendicular to the first scoremarking at its distal end, wherein the length of the first scoremarking is selected such that the two perpendicular scoremarkings divide the tablet into three equal parts and (iv) a single scoremarking on the second surface dividing the tablet into two equal parts, wherein the scoremarking on the second surface is located to extend from an angle adjacent to the edge from which the first scoremarking on the opposite side extended or located to extend from the midpoint of the same edge, from which the first scoremarking, on the opposite side extended to the midpoint of the opposite angle.

2. A tablet according to claim 1, wherein the scoremarkings have a depth of from about 1/20 to about ½ of the thickness of the tablet.

3. A tablet according to claim 1, having beveled edges and wherein the scoremarkings have an indentation depth to a line defining the beveled edges.

4. A tablet according to claim 3, wherein the beveled edge angle is in the range from about 10 to 80 degrees from the adjacent surface.

5. A tablet according to claim 4, wherein the beveled edge angle is in the range from about 30 to 60 degrees.

6. A tablet according to claim 1, wherein the scoremarkings have a V-groove angle in the range from about 40 degrees to about 120 degrees, and a groove depth of from about 1/20 to about ½ of the thickness of the tablet.

7. A tablet according to claim 1, wherein the triangular shape is free of sharp corners and edges, all corners and sides are rounded-off, and wherein all scoremarking edges and beveled.

* * * * *